US00PP16334P3

(12) United States Plant Patent
Trees

(10) Patent No.: US PP16,334 P3
(45) Date of Patent: Mar. 14, 2006

(54) ***OSTEOSPERMUM* PLANT NAMED 'BALSERWHIT'**

(50) Latin Name: *Osteospermum ecklonis*
Varietal Denomination: Balserwhit

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 128 days.

(21) Appl. No.: 11/017,551

(22) Filed: Dec. 20, 2004

(65) Prior Publication Data

US 2005/0155127 P1 Jul. 14, 2005

(51) Int. Cl.
*A01H 5/00* (2006.01)

(52) U.S. Cl. ..... Plt./360

(58) Field of Classification Search ..... Plt./360
See application file for complete search history.

*Primary Examiner*—Kent Bell
(74) *Attorney, Agent, or Firm*—Wood, Phillips, Katz, Clark & Mortimer

(57) ABSTRACT

A new and distinct cultivar of *Osteospermum* plant named 'Balserwhit' characterized by its single inflorescence form with white-colored ray florets and blue-colored disc florets, freely branching character, medium green-colored foliage, and compact and upright growth habit.

1 Drawing Sheet

Latin name of the genus and species of plant claimed: *Osteospermum ecklonis.*
Variety denomination: 'Balserwhit'.

BACKGROUND OF THE INVENTION

The present invention relates to a new and distinct cultivar of *Osteospermum* plant botanically known as *Osteospermum ecklonis,* and hereinafter referred to by the cultivar name 'Balserwhit'.

The new *Osteospermum* originated in a controlled breeding program in Arroyo Grande, Calif., during August 2001. The objective of the breeding program was the development of *Osteospermum* cultivars that are freely branching, have a compact and upright growth habit, are freely flowering, and have unique inflorescence coloration.

The new cultivar originated from the open-pollination of the cultivar Shell Beach Daisy, not patented, characterized by its lavender-colored "spoon" shaped ray florets, medium to large foliage, and limiting branching. Seed from the above stated open-pollination was germinated and grown to maturity. One plant from within the progeny was discovered and selected by the inventor during October 2002, in a controlled environment at Arroyo Grande, Calif.

Asexual reproduction of the new cultivar by terminal stem cuttings since October 2002 at West Chicago, Ill. has demonstrated that the new cultivar reproduces true to type, with all the characteristics as herein described, firmly fixed and retained through successive generations of such asexual propagation.

SUMMARY OF THE INVENTION

The following characteristics of the new cultivar have been repeatedly observed and can be used to distinguish 'Balserwhit' as a new and distinct cultivar of *Osteospermum* plant:

1. Single inflorescence form with blush white-colored ray florets and blue-colored disc florets.
2. Small, medium green-colored foliage.

3. Freely branching character.
4. Compact and upright growth habit.

Plants of the new cultivar differ from plants of the female parent primarily in inflorescence color, ray floret shape, and foliage size.

Plants of the new cultivar are most similar to 'Brightside', U.S. Plant Pat. No. 10,596. However, in side-by-side comparisons, plants of the new cultivar differ from plants of 'Brightside' in the following characteristics:

1. Plants of the new cultivar have longer leaves than plants of 'Brightside'.
2. Plants of the new cultivar have smaller inflorescences than plants of 'Brightside'.

BRIEF DESCRIPTION OF THE PHOTOGRAPHS

The accompanying photographs show, as nearly true as it is reasonably possible to make the same in color illustrations of this type, typical inflorescence and foliage characteristics of the new cultivar. Colors in the photographs differ slightly from the color values cited in the detailed description, which accurately describe the colors of the new cultivar. The plants were grown in 10 cm pots for 10 weeks in a greenhouse at West Chicago, Ill.

DETAILED BOTANICAL DESCRIPTION

Figure 1:
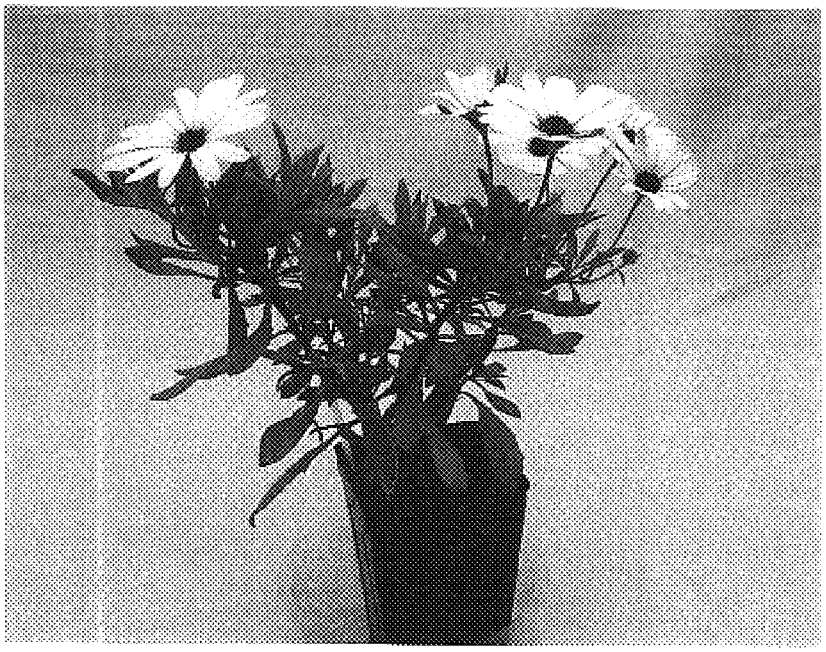
FIG. 1 illustrates a side view of the overall growth and flowering habit of the new cultivar with one plant per pot.
Figure 2:
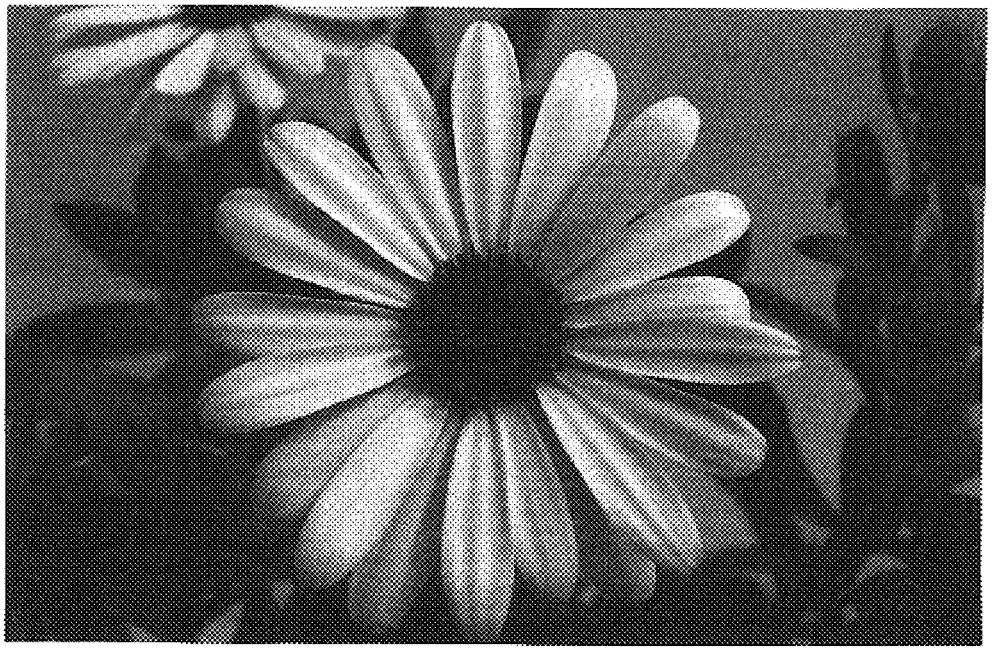
FIG. 2 illustrates a close-up view of an individual inflorescence of the new cultivar.

The new cultivar has not been observed under all possible environmental conditions to date. Accordingly, it is possible that the phenotype may vary somewhat with variations in the environment, such as temperature, light intensity, and day length without, however, any variance in genotype.

The chart used in the identification of colors described herein is The R.H.S. Colour Chart of The Royal Horticultural Society, London, England, 2001 edition, except where color terms of ordinary significance are used. The color values were determined on Sep. 24, 2004 between 1:00 and 3:00 p.m. under natural light conditions.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 14 weeks while utilizing a soilless growth medium. Greenhouse temperatures were maintained at approximately 60°–75° F. (15°–24° C.) during the day and approximately 45°–55° F. (7°–13° C.) during the night. Greenhouse light levels were maintained at 5,000 to 9,000 footcandles during the day.

Botanical classification: *Osteospermum ecklonis* cultivar Balserwhit.

Parentage: Open-pollination of the cultivar Shell Beach Daisy, not patented.

Propagation:

*Type cutting.*—Terminal stem.

*Time to initiate roots.*—Approximately 9 to 12 days.

*Time to produce a rooted cutting.*—Approximately 21–28 days.

*Root description.*—Fine, fibrous.

*Rooting habit.*—Freely branching.

Plant description:

*Crop time.*—Approximately 10–13 weeks in a 10 cm pot.

*Growth habit.*—Compact, freely branching.

*Form.*—Upright.

*Size.*—Height: Approximately 15.4 cm from soil level to top of plant plane. Width (area of spread): Approximately 20.1 cm.

*Branch.*—Quantity per plant: Approximately 4. Strength: Strong. Length from soil level to base of peduncle: Approximately 15.2 cm. Diameter: Approximately 4.4 mm. internode length at middle of branch: Approximately 6.2 mm. Texture: Glabrous. Color 145A with overlay of 187A.

*Foliage.*—Quantity per branch: Approximately 21. Type: Simple. Fragrance: Pungent. Arrangement: Alternate. Aspect: At an acute angle to the stem. Shape: Elliptic, pinnatified. Apex: Acute. Base: Attenuate, sessile. Margin: Widely dentate. Venation pattern: Pinnate. Length: Approximately 7.8 cm. Width: Approximately 2.4 cm. Texture of upper surface: Glabrous. Texture of lower surface: Glabrous with moderate pubescence along margin and veins. Color of upper surface of mature foliage: Slightly more yellow than 137A with venation of 145B. Color of lower surface of mature foliage: 146B with venation of 145B.

Flowering description:

*Time to first flower.*—Approximately 10–13 weeks from planting of rooted cutting.

*Flowering habit.*—Freely flowering under outdoor growing conditions with substantially continuous blooming from spring through autumn and year round in greenhouse environment.

*Flower arrangement.*—Solitary, terminal.

Inflorescence description:

*Appearance/type.*—Composite, persistent. Shape: Round. Aspect: Facing upward or outward. Disc and ray florets develop acropetally on a capitulum. Fragrance: None.

*Quantity of inflorescences and buds per plant.*—Approximately 5 inflorescence and 18 buds.

*Size.*—Diameter: Approximately 6.7 cm. Depth: Approximately 1.9 cm.

*Lastingness of inflorescence.*—Approximately 6–10 days.

*Bud.*—Rate of opening: Generally it takes 3–4 days for buds to progress from first color to fully open inflorescences. Shape at first color: Elliptic. Diameter: Approximately 1.2 cm. Depth: Approximately 1.9 mm. Color: Closest to N187A.

*Ray florets.*—Quantity per inflorescence: Approximately 21, arranged in a single whorl. Arrangement: Slightly overlapping. Aspect: Cupped when first open, progressing to flat then down turning at maturity. Shape: Ligulate. Apex: Emarginate. Base: Attenuate. Margin: Entire. Length: Approximately 3.4 cm. Width: Approximately 7.8 mm. Texture: Glabrous and ribbed. Color of young and mature ray florets: Upper surface: Closest to but lighter than 155D. Lower surface: Closest to 186C with ribs of N186B.

*Disc.*—Diameter: Approximately 1.2 cm. Depth: Approximately 7.8 mm. Receptacle diameter: 3.5 mm. Receptical depth: 2 mm. Receptacle color: 145B.

*Disc florets.*—Quantity per inflorescence: Approximately 60. Shape: Tubular with five lobes each having an acute apex. Margin: Entire. Length: Approximately 6 mm. Diameter at apex: Approximately 3 mm. Diameter at base: Approximately 0.8 mm. Texture of outer surface: Sparsely pubescent. Texture of inner surface: Glabrous. Color of immature floret: N92A. Color of mature floret: 77A. Calyx.

*Phyllaries.*—Quantity per inflorescence: Approximately 18. Arrangement: Imbricate, arranged in several rows. Shape: Lanceolate. Apex: Acuminate. Base: Truncate. Margin: Entire. Length: Approximately 1.1 cm. Width: Approximately 2 mm. Texture of upper surface: Glabrous, papery along edges. Texture of lower surface: Moderately pubescent. Color of upper surface: Closest to 143B. Color of lower surface: Closest to 143C. Translucent along margin.

*Peduncle.*—Strength: Strong. Aspect: Erect. Length: Approximately 5.9 cm. Diameter: Approximately 1.7 mm. Texture: Rough. Color: 144B with overlay of 187B.

*Reproductive organs.*—Androecium: Present on disc florets only. Stamen quality: 5. Anther shape: Linear. Anther length: 2 mm. Anther color: 93A. Amount of pollen: Abundant. Pollen color: 21A. Gynoecium: Present on ray and disc florets. There is one pistil per floret. Pistil length: 8 mm. Stigma shape: Two parted. Stigma length: 1 mm. Stigma color: N92A. Style length: 4 mm. Style color: N155B. Ovary diameter: 3 mm. Ovary color.

Seed and fruit production: Neither seed nor fruit production has been observed.

Disease and pest resistance: Resistance to pathogens and pests common to *Osteospermums* has not been observed.

What is claimed is:

1. A new and distinct cultivar of *Osteospermum* plant named 'Balserwhit', substantially as herein shown and described.

* * * * *